United States Patent
Reinehr et al.

(10) Patent No.: US 6,730,655 B2
(45) Date of Patent: May 4, 2004

(54) BIPHENYL DIQUATERNARY AMMONIUM COMPOUNDS

(75) Inventors: Dieter Reinehr, Kandern (DE); Dietmar Ochs, Schopfheim (DE); Hanspeter Sauter, Schopfheim (DE); Fernand Hoffstetter, Ranspach le Bas (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 332 days.

(21) Appl. No.: 09/956,318

(22) Filed: Sep. 19, 2001

(65) Prior Publication Data

US 2002/0061832 A1 May 23, 2002

(30) Foreign Application Priority Data

Sep. 21, 2000 (EP) .............................. 00810865

(51) Int. Cl.⁷ ................................. C11D 1/62
(52) U.S. Cl. ............... 510/504; 510/119; 510/123; 510/130; 510/131; 510/382; 510/384; 510/391
(58) Field of Search ................. 510/119, 123, 510/130, 131, 382, 384, 391, 504

(56) References Cited

U.S. PATENT DOCUMENTS 3,471,560 A   10/1969   Bauman .................. 260/567.6

FOREIGN PATENT DOCUMENTS

| EP | 0825175 | 2/1998 |
|---|---|---|
| WO | 200260856 | * 8/2001 |

OTHER PUBLICATIONS

J. Salvino et al., Bioorganic and Medicinal Chemistry Letters, vol. 5, No. 4, pp. 357–362 (1995).
N. Khanna et al., J. Sci. Ind. Res., vol. 14B, (1995), pp. 214–217.

* cited by examiner

Primary Examiner—Charles Boyer
(74) Attorney, Agent, or Firm—Kevin T. Mansfield

(57) ABSTRACT

There are described diquaternary ammonium compounds of the general formula:

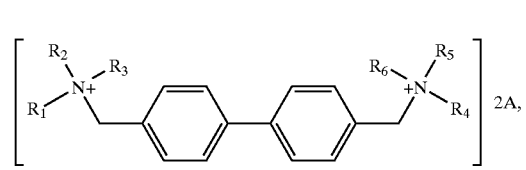

(1)

wherein $R_1$ and $R_4$ are each independently of the other $C_4$–$C_{16}$alkyl, phenyl or phenyl-$C_1$–$C_{10}$ alkyl, $R_2$, $R_3$, $R_5$ and $R_6$ are each independently of the others $C_1$–$C_4$alkyl, and A is a monovalent anion. The compounds exhibit a pronounced action against gram-positive and gram-negative bacteria, and also against yeast, molds and algae. They are accordingly suitable for the antimicrobial treatment of surfaces and for the preservation and disinfection of materials and cosmetic products, and especially also for the preparation of solid or liquid formulations and for the preservation of foodstuffs and drinks. The compounds are furthermore suitable for imparting antimicrobial properties to technical plant and for antimicrobial water treatment.

17 Claims, No Drawings

BIPHENYL DIQUATERNARY AMMONIUM COMPOUNDS

The present invention relates to new diquaternary ammonium compounds, to a process for the preparation thereof, to the use thereof as antimicrobial agents against gram-positive and gram-negative bacteria, yeasts, fungi and algae, to the use thereof as disinfectants and preservatives, and to the use thereof in the preparation of formulations for technical use, cosmetic use and use in hygiene.

The diquaternary ammonium compounds according to the invention correspond to formula:

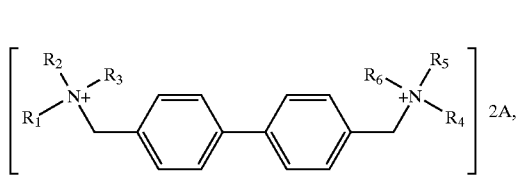

(1)

wherein $R_1$ is $C_5-C_{16}$alkyl, phenyl or phenyl-$C_1-C_{10}$alkyl, $R_4$ is $C_4-C_{16}$alkyl, phenyl or phenyl-$C_1-C_{10}$alkyl, $R_2$, $R_3$, $R_5$ and $R_6$ are each independently of the others $C_1-C_4$alkyl, and A is a monovalent anion, with the proviso that when $R_1$ and $R_4$ are benzyl and $R_2$, $R_3$, $R_5$ and $R_6$ are identical and are methyl or n-propyl, A is not $Br^-$ or $I^-$.

$C_4-C_{16}$Alkyl radicals are unbranched or branched alkyl radicals, for example n-butyl, sec-butyl, tert-butyl, pentyl, hexyl, octyl, decyl, dodecyl or hexadecyl.

$C_5-C_{16}$Alkyl radicals are unbranched or branched alkyl radicals, for example pentyl, hexyl, octyl, decyl, dodecyl or hexadecyl.

Phenyl-$C_1-C_{10}$alkyl is, for example, benzyl, phenethyl, phenylpropyl, phenylisopropyl, phenylbutyl, phenyl-sec-butyl, phenyl-tert-butyl or phenyldecyl.

$C_1-C_4$Alkyl radicals are unbranched or branched alkyl radicals, for example methyl, ethyl, propyl, isopropyl, n-butyl, sec-butyl or tert-butyl.

A is a monovalent anion, for example a halide anion, such as $F^-$, $Cl^-$, $Br^-$ or $I^-$, or an inorganic or organic group, for example hydrogen carbonate, nitrate, hydrogen sulfate, chlorate, dihydrogen phosphate, formate, acetate, or p-toluene hydrogen sulfate. Preferred as halide anion is $Cl^-$.

The identities of substituents $R_1$, $R_2$, $R_3$, $R_4$, $R_5$ and $R_6$ may each be independent of the others and have the meanings given. Preference is given to diquaternary ammonium compounds in which $R_4$ and $R_1$, $R_5$ and $R_2$, and $R_6$ and $R_3$ are identical, in accordance with formula (1'):

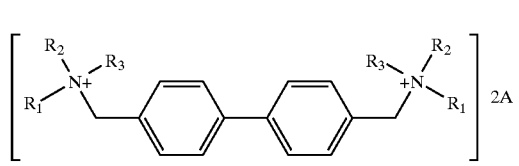

(1')

Of interest are compounds of formula (1') wherein $R_1$ is $C_5-C_{16}$alkyl, preferably unbranched $C_5-C_{16}$alkyl, and especially $C_6$-, $C_8$-, $C_{12}$- or $C_{16}$-alkyl.

Also of interest are compounds of formula (1') wherein $R_2$ and $R_3$ are each independently of the other unbranched $C_1-C_4$alkyl, especially a $CH_3$ group.

Of special interest are the mentioned compounds of formula (1') wherein A is a halide anion, especially $Cl^-$, preferably according to the following formulae:

(2)

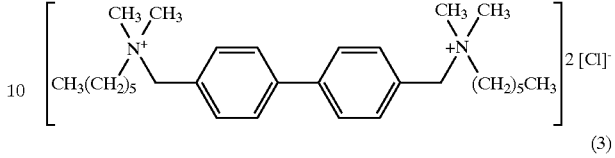

(3)

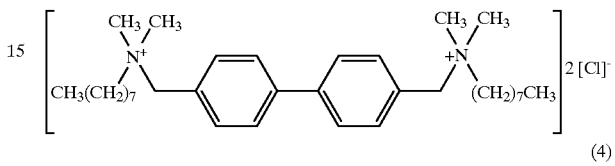

(4)

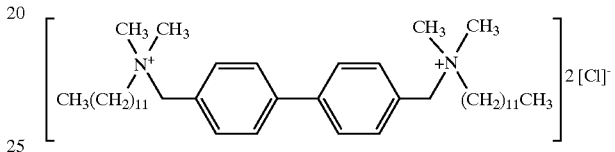

and (5)

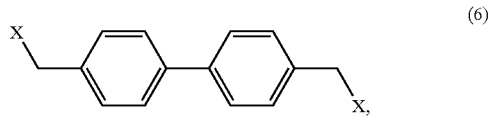

The process according to the invention for the preparation of diquaternary ammonium compounds of formulae (1) and (1') comprises a quaternisation reaction of a biphenyl compound of formula:

(6)

wherein X is halogen, such as fluorine, chlorine, bromine or iodine, or a monovalent, inorganic or organic, anion-forming leaving group, for example —$CO_3H$, —$NO_3$, —$SO_4H$, —$ClO_3$, —$PO_4H_2$, —COOH, —$COOCH_3$ or —$SO_3(C_6H_4)CH_3$, with an amino compound of formula (7)

$R_1-N\begin{smallmatrix}R_2\\R_3\end{smallmatrix}$, wherein $R_1$, $R_2$ and $R_3$ are each independently of the others as defined hereinbefore, and with a further amino compound of formula

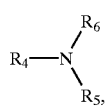

wherein
$R_4$, $R_5$ and $R_6$ are each independently of the others as defined hereinbefore.

In the general process for the preparation of the diquaternary ammonium compound of formula (1), the reaction of the biphenyl compound (6) is carried out with two different amino compounds (7) and (8), which can result in a mixture of up to three different products which, if desired, can be separated, for example by chromatographic methods.

In the process for the preparation of the diquaternary ammonium compound of formula (1'), the reaction of the biphenyl compound (6), for example with an amino compound of formula (7), is carried out preferably in a polar solvent, with heating, there being possible as solvent, for example, water, an alcohol, for example MeOH, EtOH or isopropanol, a ketone, for example acetone, or DMF, DMSO, or a mixture of two or more such solvents. The amino compound (7) is preferably used in stoichiometric ratio or in stoichiometric excess relative to the biphenyl compound (6). Especially suitable amino compounds of formula (7) are those in which $R_1$ is unbranched $C_5-C_{16}$alkyl and $R_2$ and $R_3$ are each a $CH_3$ group. For example, N,N'-dimethylhexylamine is introduced into water and heated to approximately from 60 to 90° C. The biphenyl compound of formula (6), wherein X is preferably halogen and is especially —Cl, for example bis(chloromethyl) biphenyl, in a suitable solvent, for example isopropanol, is metered in in the course of approximately from 40 to 80 minutes. After stirring for a relatively long period (for example approximately 2 hours), the isopropanol is distilled off at approximately from 80 to 110° C., water simultaneously being added dropwise to the mixture. After concentration, the residue is brought to dryness in vacuo, yielding the diquaternary ammonium compound which, in the example mentioned, corresponds to formula (2). Further details relating to the preparation process according to the invention are given in the corresponding Examples.

The biphenyl compounds of formula (6) used in the preparation process are known or can be prepared in a manner known per se; for example they can be prepared according to the Blanc chloromethylation reaction from biphenyl, formaldehyde, and HCl in the presence of $ZnCl_2$ (e.g. DE-A-1 793 482).

The present invention relates also to the use, as antimicrobial agents, disinfectants and preservatives, of diquaternary ammonium compounds of formula:

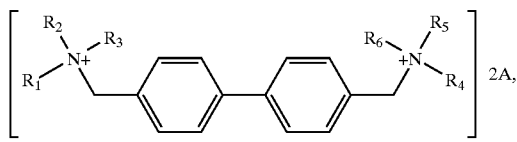

wherein
$R_1$ and $R_4$ are each independently of the other $C_4-C_{16}$alkyl, phenyl or phenyl-$C_1$-$C_{10}$alkyl,
$R_2$, $R_3$, $R_5$ and $R_6$ are each independently of the others $C_1-C_4$alkyl, and A is a monovalent anion.

The diquaternary ammonium compounds exhibit pronounced antimicrobial action, especially against gram-positive and gram-negative bacteria, against bacteria of the skin flora, against yeasts and moulds, and also against algae. They are accordingly suitable as antimicrobial agents, as disinfectants and as preservatives.

They are suitable especially for disinfection, deodorisation, and for general and antimicrobial treatment of the skin, mucosa and hair, more especially for the disinfection of hands, wounds and the throat. It has furthermore been demonstrated that, even at low concentrations, the antimicrobial activity is still assured.

They are also suitable for use in solid or liquid formulations, such as personal care preparations, shampoos, bath additives, haircare preparations, cosmetic and medicinal soaps, lotions, creams, deodorants, or cleansing solutions, for cleaning or rinsing solutions, for example for oral use in the household sector and in the hygiene sector, for example hospitals, retirement homes or doctors' surgeries, and for use in cleaning and disinfecting preparations for surfaces in the household sector, in industry and in the hygiene sector.

They are furthermore suitable for imparting antimicrobial properties to technical plant, such as cooling systems, paper treatment machines and swimming pools, and for antimicrobial water treatment for the purpose of reducing the growth of bacteria, fungi and algae and for controlling slime. In addition, they are suitable for the preservation of materials, for example filter materials for air and water filters, textile fibre materials, for example cellulose fibres, cotton, silk, wool, polyamide fibres, plastics, for example dressing materials, catheters and syringes, and for the preservation of paper, wood, leather, paints and surface coatings. They are furthermore suitable for the preservation of foodstuffs or drinks, for example beer.

Some of the mentioned applications for the preparation of formulations are listed hereinbelow:

A disinfectant preparation for the hands has, for example, the following composition:
  0.01 to 5% by weight of a compound of formula (1)
  60% by weight isopropanol
  0.1% by weight perfume oil, and
  water ad 100%.

A personal care preparation contains, for example, from 0.01 to 15% by weight, preferably from 0.1 to 10% by weight, based on the total weight of the composition, of a diquaternary ammonium compound of formula (1) and cosmetically tolerable adjuvants.

Depending upon the form of the personal care preparation, it comprises, in addition to the diquaternary ammonium compound of formula (1), further constituents, such as sequestering agents, colourings, perfume oils, thickening or solidifying agents (consistency regulators), emollients, UV-absorbers, skin protective agents, antioxidants, additives that improve the mechanical properties, such as dicarboxylic acids and/or aluminium, zinc, calcium or magnesium salts of $C_{14}-C_{22}$fatty acids, and, optionally, preservatives.

The personal care preparation may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations can be used in various fields. There come into consideration, for example, especially the following preparations:

- skin-care preparations, e.g. skin-washing and cleansing preparations in the form of tablet-form or liquid soaps, synthetic detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- intimate hygiene preparations, e.g. intimate washing lotions or intimate sprays;
- foot-care preparations, e.g. foot baths, foot powders, foot creams or foot balsams, special deodorants and anti-perspirants or callus-removing preparations;
- light-protective preparations, such as sun milks, lotions, creams or oils, sun-blocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de parfum, parfum de toilette, perfume), perfume oils or perfume creams;
- dental care, denture-care and mouth-care preparations, e.g. toothpastes, gel toothpastes, tooth powders, mouthwash concentrates, anti-plaque mouthwashes, denture cleaners or denture fixatives;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:

0.01 to 5% by weight of a compound of formula (1)

0.3 to 1% by weight titanium dioxide, 1 to 10% by weight stearic acid, soap base ad 100%, e.g. a sodium salt of tallow fatty acid or coconut fatty acid, or glycerol.

A shampoo has, for example, the following composition:

0.01 to 5% by weight of a compound of formula (1), 12.0% by weight sodium laureth-2-sulfate, 4.0% by weight cocamidopropyl betaine, 3.0% by weight NaCl and water ad 100%.

A deodorant has, for example, the following composition:

0.01 to 5% by weight of a compound of formula (1),

60% by weight ethanol, 0.3% by weight perfume oil, and water ad 100%.

An oral composition contains, for example, from 0.01 to 15% by weight, based on the total weight of the composition, of a compound of formula (1), and orally tolerable adjuvants.

Example of an oral composition:

10% by weight sorbitol,

10% by weight glycerol,

15% by weight ethanol,

15% by weight propylene glycol, 0.5% by weight sodium lauryl sulfate, 0.25% by weight sodium methylcocyl taurate, 0.25% by weight polyoxypropylene/polyoxyethylene block copolymer, 0.10% by weight peppermint flavouring, 0.1 to 0.5% by weight of a compound of formula (1), and 48.6% by weight water.

The oral composition may be, for example, in the form of a gel, a paste, a cream or an aqueous preparation (mouthwash).

The oral composition may also comprise compounds that release fluoride ions which are effective against the formation of caries, for example inorganic fluoride salts, e.g. sodium, potassium, ammonium or calcium fluoride, or organic fluoride salts, e.g. amine fluorides.

The compounds can be used especially in household and general-purpose cleaners for cleaning and disinfection, and for disinfecting hard surfaces.

A cleaning preparation has, for example, the following composition:

0.01 to 5% by weight of a compound of formula (1)

3.0% by weight octyl alcohol 4 EO 1.3% by weight fatty alcohol $C_8$–$C_{10}$polyglucoside
3.0% by weight isopropanol
water ad 100%.

A general purpose cleaner has, for example, the following composition:
0.01 to 5% by weight of a compound of formula (1)
2.9% by weight cocamidopropyl betaine
3.0% by weight lauramine oxide
4.2% by weight sodium lauryl ether sulfate
4.0% by weight sodium citrate
3.0% by weight sodium carbonate
3.0% by weight ethanol
water ad 100%.

An all-purpose cleaner has, for example, the following composition:
0.1 to 5% by weight of a compound of formula (1)
2.0% by weight cocamidopropyl betaine
3.0% by weight lauramine oxide
6.0% by weight lauryl alcohol 9 EO
4.0% by weight sodium citrate
3.0% by weight sodium carbonate
5.0% by weight sodium cumenesulfonate
3.0% by weight ethanol
water ad 100%.

A bathroom cleaner has, for example, the following composition:
0.01 to 5% by weight of a compound of formula (1)
1.7% by weight octyl alcohol 4 EO
3.5% by weight fatty alcohol $C_8$–$C_{10}$polyglucoside
4.8% by weight citric acid
4.0% by weight acetic acid
water ad 100%.

A dishwashing agent has, for example, the following composition:
0.1 to 5% by weight of a compound of formula (1)
15.0% by weight fatty alcohol $C_8$–$C_{10}$polyglucoside
7.0% by weight lauryl alcohol 9 EO
5.0% by weight sodium cumenesulfonate
3.0% by weight citric acid
1.0% by weight sodium chloride
3.5% by weight sodium sulfate
water ad 100%.

A further dishwashing agent has, for example, the following composition:
0.01 to 5% by weight of a compound of formula (1)
10.0% by weight sodium $C_{14}$–$C_{17}$alkyl-sec-sulfonate
20.0% by weight fatty alcohol $C_8$–$C_{10}$polyglucoside
3.0% by weight lauryl alcohol 9 EO
5.0% by weight sodium cumenesulfonate
3.0% by weight citric acid
water ad 100%.

The following Examples illustrate the invention. Unless otherwise indicated, parts are parts by weight.

Examples of the synthesis of the diquaternary ammonium compounds of formulae (2) to (4):

EXAMPLE 1
4,4'-Bis(N,N-dimethyl-N-hexyl-ammoniummethyl)biphenyl dichloride (2)

25.85 g of N,N'-dimethylhexylamine (0.208 mol) are emulsified in approximately 50 ml of water and the emulsion is heated to approximately 75° C. A suspension of 25.1 g of 4,4'-bis(chloromethyl)biphenyl (0.1 mol) in 150 ml of isopropanol is then metered in in the course of 1 hour, during which the pH value of the mixture falls from an initial 9.4 to 7.3. The mixture is stirred for about 2 hours at approximately 75 to 81° C., and the isopropanol is then distilled off with heating at approximately from 81 to 100° C., 300 ml of water continuously being added dropwise to the mixture at the same time. The yellowish solution is adjusted to a weight of 510 g by the addition of water (corresponding to a 10% solution). Half of the solution is brought to dryness in vacuo after concentration. The residue is pulverised to yield 26.6 g of a whitish powder.

Elemental analysis yields the following values for $C_{30}H_{50}N_2Cl_2$:

|  | C | H | N | Cl | $H_2O$ |
| --- | --- | --- | --- | --- | --- |
| calculated: | 70.42% | 10.24% | 5.47% | 13.86% | — |
| found: | 67.4% | 9.9% | 5.2% | 13.7% | 3.4% |

EXAMPLE 2
4,4'-Bis(N,N-dimethyl-N-octyl-ammoniummethyl)biphenyl dichloride (3):

The procedure is as described in Example 1, an equimolar amount of N,N'-dimethyl-octylamine being used instead of N,N'-dimethylhexylamine.

EXAMPLE 3
4,4'-Bis(N,N-dimethyl-N-dodecyl-ammoniummethyl)biphenyl dichloride (4):

The procedure is as described in Example 1, an equimolar amount of N,N'-dimethyl-dodecylamine being used instead of N,N'-dimethylhexylamine.

EXAMPLE 4
4,4'-Bis(N,N-dimethyl-N-hexadecyl-ammoniummethyl)biphenyl dichloride (5):

The procedure is as described in Example 1, an equimolar amount of N,N'-dimethyl-hexadecylamine being used instead of N,N'-dimethylhexylamine.

In each of the four Examples a whitish powder is obtained.

Determination of the Minimum Inhibitory Concentration (MIC Value)

The procedure to determine the antimicrobial activity of the compounds of the invention is as follows:

Nutrient
- Casein/soybean flour peptone bouillon for the preparation of pre-cultures of the test bacteria and yeast.
- Sabouraud agar for the pre-culture of Aspergillus niger.
- Mueller Hinton agar for determining the MIC value of bacteria.
- Sabouraud agar for determining the MIC value of Aspergillus niger and Candida albicans.
- deionised water or EtOH as solvent.

| Examples of test organisms | |
| --- | --- |
| bacteria: | *Staphylococcus hominis* DSM 20328 |
| | *Escherichia coli* NCTC 8196 |

-continued

| Examples of test organisms | |
|---|---|
| yeast: | *Candida albicans* ATCC 10231 |
| mould: | *Aspergillus niger* ATCC 6275 |

Procedure

The test substances are predissolved in deionised water or in ethanol and incorporated in a dilution series in agar warmed to 47–50° C.

The mould is cultured on Sabouraud agar and rinsed off with 0.85% sodium chloride solution containing 0.01% Triton X-100.

Bacteria and yeast are incubated for from 18 to 24 hours at 37° C. in casein/soybean flour peptone bouillon.

All the test organisms are adjusted to an organism count of from $10^6$ to $10^7$ CFU/ml using 0.85% sodium chloride solution.

The organism suspensions are each pipetted in an amount of 10 μl onto an agar plate containing the test substance. The test batches are then incubated for 2 days at 37° C. (bacteria and yeast) or for 3 days at 28° C. (*Aspergillus niger*). In order to check the influence of the solvent used (deionised water, ethanol), organism suspensions are in addition incubated on agar plates without test substances (control plates).

After incubation, the growth of the microorganisms on the test substances is compared with the control plates. The minimum inhibitory concentration (MIC value) is the concentration of substance at which (compared with the control plates) a clear inhibition of growth of the test organisms is to be ascertained.

The microbiological data ascertained are compiled in Table 1.

TABLE 1

| MIC values in ppm for different microorganisms | | | | |
|---|---|---|---|---|
| Compound of formula | S. hominis | E. coli | C. albicans | A. niger |
| (2) | 50 | 5 | 50 | 2.5 |
| (3) | 5 | 1 | 10 | 2.5 |
| (4) | 10 | 250 | 25 | 100 |
| (5) | 100 | 1000 | 500 | 1000 |

Suspension Test to Determine the Bactericidal Activity in Accordance with the European Standard According to EN 1276

Test Organisms

Staphylococcus aureus ATCC 6538.

Test Substances 2000 ppm of a solution of a compound of formula (2) and (3) in sterile, deionised water.

Contact Time 5 minutes at 20° C. (+/−1° C.).

Inactivation Medium After the Contact Time

D/E neutralisation solution (Dey-Engley, consisting of 0.1% sodium thioglycolate, 0.6% sodium thiosulfate, 0.5% Tween 80, and also 0.7% lecithin and sterile, deionised water ad 100%).

Nutrient Medium

Casein/soybean flour peptone agar with lecithin, L-histidine, and Tween 80 as inactivating agent (Merckoplate No. 18360, Merck-Darmstadt).

Incubation of the Test Plates 24 to 48 hours at 37° C.

Precaration of the Pre-Culture

The bacteria cultures are cultured on casein/soybean flour peptone slant agar and incubated for from 18 to 24 hours at 37° C. They are then rinsed off with water and adjusted to a bacteria count of $1.5 \times 10^8$–$5 \times 10^8$ CFU/ml.

Procedure

All of the reagents required for the test are first equilibrated at 20° C. (+/−1° C.). 1.0 ml of 0.3% bovine serum albumin (in deionised water) is introduced into a test tube. After the addition of 1.0 ml of bacteria suspension ($1.5 \times 10^8$–$5 \times 10^8$ CFU/ml), the solution is mixed and maintained at 20° C. for 2 minutes (+/−10 seconds). 8.0 ml of the test substance (2000 ppm solution in water) are then added. The mixture is incubated for 5 minutes at 20° C. (+/−1° C.). Subsequently, in each case 1.0 ml of the mixture is introduced into a small tube containing 8.0 ml of inactivating medium (D/E neutralisation solution) and 1.0 ml of deionised water. The mixture is then maintained at 20° C. (+/−1° C.) for 5 minutes (+/−10 seconds) and subsequently 1.0 ml thereof is transferred into a Petri dish and mixed with 15 ml of molten casein/soybean flour peptone agar containing 3% Tween 80, 0.3% lecithin and 0.1% L-histidine. The agar plates are incubated for from 24 to 48 hours at 37° C. (+/−1° C.). After the period of incubation, the number of colonies is counted and quoted as a logarithmic reduction (log 10) of the bacteria. The results are compiled in Table 2.

TABLE 2

Suspension test according to EN 1276 with *Staphylococcus aureus*

Concentration of the test substance in each case: 1600 ppm
Contact time: 5 minutes in each case
Logarithmic reduction, quoted value in log 10

| Compound of formula | Staphylococcus aureus |
|---|---|
| (2) | 5.6 |
| (3) | 5.6 |

What is claimed is:

1. A diquaternary ammonium compound of formula:

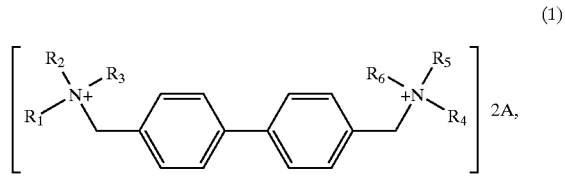

(1)

wherein $R_1$ is $C_5$–$C_{16}$alkyl, phenyl or phenyl-$C_1$–$C_{10}$alkyl, $R_4$ is $C_4$–$C_{16}$alkyl, phenyl or phenyl-$C_1$–$C_{10}$alkyl, $R_2$, $R_3$, $R_5$ and $R_6$ are each independently of the others $C_1$–$C_4$alkyl, and A is a monovalent anion, with the proviso that when $R_1$ and $R_4$ are benzyl and $R_2$, $R_3$, $R_5$ and $R_6$ are identical and are methyl or n-propyl, A is not Br⁻ or I⁻.

2. A diquaternary ammonium compound according to claim 1, wherein $R_4$ and $R_1$, $R_5$ and $R_2$, and $R_6$ and $R_3$ are identical, and wherein A is a halide anion or an inorganic or organic anionic group.

3. A diquaternary ammonium compound according to claim 1, wherein $R_1$ is $C_5$–$C_{16}$alkyl.

4. A diquaternary ammonium compound according to claim 1, wherein $R_1$ is unbranched $C_5$–$C_{16}$alkyl.

5. A diquaternary ammonium compound according to claim 1, wherein $R_2$ and $R_3$ are each independently of the other unbranched $C_1$–$C_4$alkyl.

6. A diquaternary ammonium compound according to claim 1, wherein A is.

7. A diquaternary ammonium compound according to claim 1, of formula:

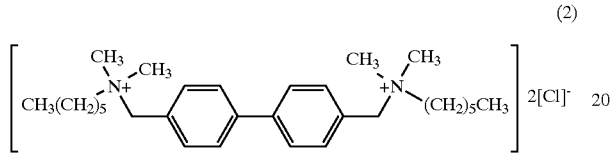
(2)

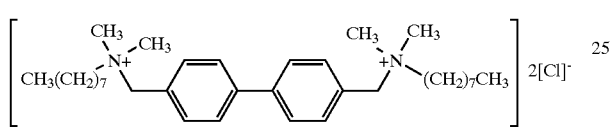
(3)

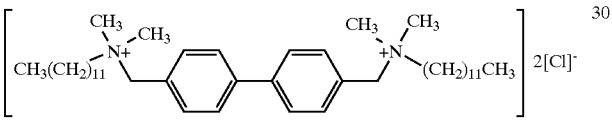
(4)

or

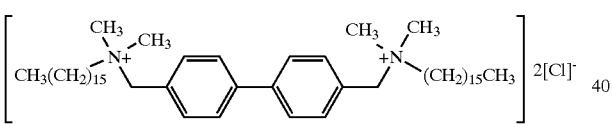
(5)

8. A process for the preparation of a diquaternary ammonium compound according to claim 1, wherein a biphenyl compound of formula:

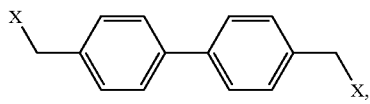
(6)

wherein X is halogen or a monovalent, inorganic or organic, anion-forming group, is reacted in a quaternisation reaction with an amino compound of formula:

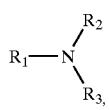
(7)

wherein $R_1$, $R_2$ and $R_3$ are each independently of the others as defined in claim 1, and with a further amino compound of formula:

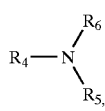
(8)

wherein $R_4$, $R_5$ and $R_6$ are each independently of the others as defined in claim 1.

9. A personal care composition, which comprises
0.01 to 15% by weight a diquaternary ammonium compound of the formula (1) according to claim 1 and a cosmetically tolerable adjuvant therefor.

10. An oral personal care composition according to claim 9, which comprises
0.01 to 15% by weight a diquaternary ammonium compound of the formula (1) according to claim 1 and an orally tolerable adjuvant therefor.

11. A personal care composition according to claim 9, which is a skin-care preparation, a bath preparation, a cosmetic personal care preparation, an intimate hygiene preparation, a foot-care preparation, a light-protective preparation, a skin-tanning preparation, an insect-repellent, an antiperspirant, a chemical hair-removal preparation, a shaving preparation, a fragrance preparation, a dental care preparation or a cosmetic hair-treatment preparation.

12. A disinfectant composition, which comprises
0.01 to 5% by weight a diquaternary ammonium compound of the formula (1) according to claim 1 and a carrier therefor.

13. A method of controlling pathogens selected from gram-positive and gram-negative bacteria, yeasts, moulds and algae, which comprises contacting said patogens with an effective cleaning and disinfecting amount of a diquaternary ammonium compound of the formula (1) according to claim 1.

14. A method of cleaning and disinfecting a substrate, which comprises contacting said substrate with an effective cleaning and disinfecting amount of a diquaternary ammonium compound of the formula (1) according to claim 1.

15. A method according to claim 14, where the substrate is skin, mucosa or hair.

16. A method according to claim 14, where the substrate is a hard surface.

17. A method of imparting antimicrobial properties to an aqueous liquid, which comprises contacting said liquid with an antimicrobially effective amount of a diquaternary ammonium compound of the formula (1) according to claim 1.

* * * * *